United States Patent [19]

Miller et al.

[11] Patent Number: 4,967,590
[45] Date of Patent: Nov. 6, 1990

[54] SUPERCRITICAL FLUID CHROMATOGRAPHY INJECTOR AND THE METHOD FOR USING THE SAME

[75] Inventors: David J. Miller; Steven B. Hawthorne, both of Grand Forks, N. Dak.

[73] Assignee: UND-SEM Foundation, Grand Forks, N. Dak.

[21] Appl. No.: 408,609

[22] Filed: Sep. 18, 1989

[51] Int. Cl.⁵ ..................... G01N 30/12; G01N 30/20; G01N 30/18

[52] U.S. Cl. ................. 73/23.41; 73/864.84; 73/864.87

[58] Field of Search ............... 73/864.81, 864.87, 23.1, 73/61.1 C, 23.35–23.42, 23.22–23.27; 422/70, 89; 432/161

[56] References Cited

U.S. PATENT DOCUMENTS

| | | | |
|---|---|---|---|
| 3,118,300 | 1/1964 | Jenkins | 73/864.84 |
| 3,223,123 | 12/1965 | Young | 137/25.46 |
| 3,223,747 | 12/1965 | Bohrer | 260/647 |
| 3,352,644 | 11/1967 | Lysyj | 422/89 X |
| 3,475,950 | 11/1969 | Fesian | 73/864.83 |
| 3,630,371 | 12/1971 | Hrdina | 210/198 |
| 3,675,466 | 7/1972 | Linenberg | 422/89 X |
| 3,733,908 | 5/1973 | Linenberg | 73/864.83 X |
| 4,042,499 | 8/1977 | Ramstad et al. | 210/31 C |
| 4,137,161 | 1/1979 | Shimada et al. | 210/31 C |
| 4,158,630 | 6/1979 | Stearns | 210/198 C |
| 4,187,177 | 2/1980 | Stahl | 210/198 C |
| 4,222,412 | 9/1980 | Carle | 137/625.46 |
| 4,300,393 | 11/1981 | Stearns | 73/864.84 X |
| 4,477,266 | 10/1984 | Yarg et al. | 55/67 |
| 4,479,380 | 10/1980 | Novotny et al. | 73/23.1 X |
| 4,681,678 | 7/1987 | Leaseburge et al. | 210/198.2 X |
| 4,871,453 | 10/1989 | Kumar | 210/137 X |
| 4,872,334 | 10/1989 | Watanabe | 422/89 X |

FOREIGN PATENT DOCUMENTS

| | | | |
|---|---|---|---|
| 3729775 | 3/1989 | Fed. Rep. of Germany | 73/23.1 |
| 55-76948 | 6/1980 | Japan | 422/89 |
| 62-148855 | 7/1987 | Japan | 73/61.1 C |
| 62-218860 | 9/1987 | Japan | 73/61.1 C |
| 1000904 | 2/1983 | U.S.S.R. | 422/89 |

OTHER PUBLICATIONS

"Sample-Extrusion Apparatus for High-Pressure Vapor-Liquid Equilibrisa", published circa 1969; 4 pages, by B. L. Rogers et al.; in 4/22/89.

P. A. Peaden, J. C. Fjeldsted, M. L. Lee, S. R. Springston, and M. Novotny. Instrumental aspects of capillary supercritical fluid chromatography. Anal. Chem. 54: 1090–93, Jun. 1982.

B. E. Richter, D. E. Knowles, M. R. Andersen, N. L. Porter, E. R. Campbell, and D. W. Later, Reproducibility in capillary supercritical fluid chromatography:

(List continued on next page.)

Primary Examiner—Tom Noland
Attorney, Agent, or Firm—Zarley, McKee, Thomte, Voorhees & Sease

[57] ABSTRACT

An injector for use with a capillary supercritical fluid chromatography (SFC) apparatus includes an operable four-port switching valve having a body portion and a rotor rotatably mounted within the body portion. The rotor has a hole therethrough which will selectively register with pairs of aligned ports. Thus, the rotor is rotatable between a loading position, wherein a first and third port are in communication, and a chromatographic position, wherein a second and fourth port are in communication. A first tubular member extends from the third port and is connected to a retention gap, which is in turn connected to an end of a capillary SFC column. A bypass tube connects the fourth port to the first tubular member. The loading position of the rotor and the first tubular member form a straight pathway to permit a needle to be inserted therethrough into the retention gap to inject a sample. A method is also disclosed whereby said injector permits the venting of a sample solvent from the injector by cycling the rotor, between the chromatographic and loading positions for predetermined time intervals.

8 Claims, 2 Drawing Sheets

OTHER PUBLICATIONS comparison of injection techniques. HRC & CC 11: 29–32 Jan. 1988.

T. Greibrokk, B. E. Berg, A. L. Blilie, J. Doehl, A. Farbrot, and E. Lundanes. Techniques and applications in supercritical fluid chromatography. J. Chromatogr. 394: 429–41 (1987).

R. D. Smith and H. R. Udseth. Mass spectrometer interface for microbore and high flow rate capillary supercritical fluid chromatography with splitless injection. Anal. Chem. 59: 13–22, Jan. 1987.

J. Kohler, A. Rose, and G. Schomburg. Instrumentation for SFC systems: different sampling and restriction designs. HRC & CC 11: 191–97, Feb. 1988.

J. D. Pinkston, G. D. Owens, L. J. Burkes, T. E. Delaney, D. S. Millington, and D. A. Maltby. Capillary supercritical fluid chromatography/mass spectrometry using a high mass quadrupole and splitless injection. Anal. Chem. 60: 962–66, Norlo, May 1988.

W. P. Jackson, K. E. Markides, and M. L. Lee. Supercritical fluid injection of high molecular weight polycyclic aromatic compounds in capillary supercritical fluid chromatography. HRC & CC 9: 213–17, Apr. 1986.

A. Farbrot Buskhe, B. E. Berg, O. Gyllenhaal, and T. Greibrokk. Splitless injection in capillary supercritical fluid chromatography. HRC & CC 11: 16–20, Jan. 1988.

S. L. Pentoney, Jr., A. Giorgetti, and P. R. Griffiths. Combined gas and supercritical fluid chromatography for the high resolution separation of volatile and nonvolatile compounds. J. Chromatogr. Sci. 25: 93–98, Mar. 1987.

E. J. Guthrie and H. E. Schwartz. Integral pressure restrictor for capillary SFC. J. Chromatogr. Sci. 24: 236–41 Jun. 1986.

S. B. Hawthorne and D. J. Miller. Analysis of commercial waxes using capillary supercritical fluid chromatography/mass spectrometry. J. Chromatogr. 388: 397–409 (1987).

SUPERCRITICAL FLUID CHROMATOGRAPHY INJECTOR AND THE METHOD FOR USING THE SAME

TECHNICAL FIELD

This invention generally relates to a supercritical fluid chromatography injector and a method for using the injector.

BACKGROUND OF THE INVENTION

The accuracy and range of analysis of capillary supercritical fluid chromatography (SFC) is affected by the type of injector utilized and the method for using the same. A high performance liquid chromatographic (HPLC) injector having a sample splitter is the most frequently used injector for capillary SFC. While this type of HPLC injector is useful for many applications, there are a number of drawbacks associated with the injector and the current methods for using the injector.

One drawback is that the samples must be relatively concentrated, which can be difficult to obtain for trace analytes or for samples having limited solubilities in appropriate solvents The use of a sample splitter presents the problems of: (1) splitter discrimination; (2) plugging due to the fact that the sample injector uses small sample loops which are easily plugged; and (3) a relatively large volume of the sample is needed for flushing and filling the sample loop prior to the injection.

Splitless injection techniques using HPLC-type injectors with a small sample loop—with a typical volume of 60nL—or very rapid injection techniques have also been described and used with capillary SFC. The use of splitless injection techniques are generally limited to small injection volumes and can result in unacceptably broad solvent peaks. The use, however, of post-injection solvent venting can dramatically reduce solvent tailing.

Similar to capillary gas chromatography (GC), on-column injections are expected to eliminate the possibility of splitter discrimination and to improve the ability of SFC to analyze more dilute samples while requiring less total volume for sample injection by eliminating the need to flush a sample loop. The construction of an on-column injector is far more complicated for SFC than for GC, both because capillary SFC columns have typical inner diameters of only 50 to 100 $\mu$m, and because higher pressures are used in SFC.

Early attempts to use on-column injections have involved large diameter (300 $\mu$m i.d.) columns or dipping the column into the sample solution The present invention is directed to a simple modification which can be made to a commercially available four-port valve that allows injection volumes as large as .5$\mu$L to be placed inside a short retention gap at the head of a 50 $\mu$m i.d. capillary SFC column. Also disclosed herein is a method for using the present invention which permits solvent venting with the modified apparatus, which is accomplished in a few simple steps.

The development of the injector and the development of the method for solvent venting required that a number of special concerns be addressed. One concern was that, because the chromatographic oven was held at temperature (typically 125° C.), the column's stationary phase could be exposed to atmospheric oxygen and result in degradation of the column's performance. Another concern was the possible loss of volatile analytes during the solvent venting step. Also, because the sample is injected into a retention gap with a relatively large volume of solvent, refocusing of the analytes in the chromatographic stationary phase was thought to be necessary in order to obtain good chromatographic peak shapes.

The present invention does not require the use of a sample loop, and the injection is performed with a conventional GC on-column syringe. The use of a GC on-column syringe for injection reduces sample waste compared to the injection techniques that utilize sample loops. Additionally, the present invention facilitates the use of solvent venting techniques. The use of solvent venting eliminates solvent tailing and yields chromatographic base lines comparable to those achieved using conventional split injection. Also, the use of solvent venting reduces the requirement for flushing the column between analytical runs and thus reduces the wait for the column to return to a condition suitable to begin the next analysis.

It is therefore a principal object of the present invention to provide an improved injector for use with capillary SFC analysis.

Another object of the present invention is to provide an injector which permits the use of less concentrated samples having trace analytes.

Still another object is to provide an injector which permits the use of samples having limited solubilities in appropriate solvents.

A further object of the present invention is to provide an injector which eliminates splitter discrimination and which eliminates the use of small sample loops.

Yet another object is to provide an injector which is not subject to plugging.

Another object of the present invention is to permit almost on-column injection of a sample into a capillary SFC column.

Another general object of the present invention is to provide a method for using an injector which eliminates solvent tailing.

These and other objects will become apparent to those of ordinary skill in the art.

SUMMARY OF THE INVENTION

An injector for use with a capillary supercritical fluid chromatography (SFC) apparatus is formed from a switching valve having first, second, third and fourth ports around its periphery. A rotatable rotor, having a hole extending therethrough, is mounted in the valve so that the hole selectively registers with either the first and third ports or the second and fourth ports. The rotor is rotatable between a loading position wherein the first and third ports are in communication, and a chromatographic position wherein the second and fourth ports are in communication. An upper needle guide is secured to the first port, and a pressurized supercritical fluid source is secured to the second port. A first tubular member extends from the third port and is sealably secured to a first fitting. The first fitting has an axial bore extending therethrough and a transverse aperture in communication with the bore. A bypass tube is secured between the first fitting aperture and the fourth port. A needle guide is mounted within the bore of the first fitting, and a second fitting is secured to the first fitting to retain the needle guide there. A retention gap is mounted within a bore in the second fitting, and the lower end thereof is operatively attached to a capillary SFC column.

A method for using the injector of the present invention is disclosed wherein the solvent is vented from a sample being analyzed, by rotating the rotor between the loading position and the chromatographic position.

BRIEF DESCRIPTION OF THE PREFERRED EMBODIMENT

Figure 1:
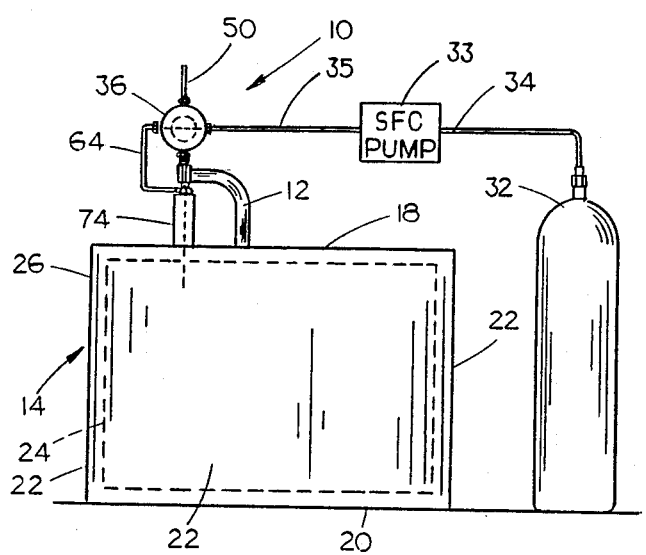
FIG. 1 is a pictorial view of the invention attached to a capillary SFC device.

Referring now to the drawings in which identical or corresponding parts are identified by the same reference numeral, the injector of this invention is identified generally at 10. The injector 10 is secured to a bracket 12 which is mounted to a supercritical fluid chromatograph 14. The supercritical fluid chromatograph 14 includes a top wall 18, a bottom wall 20, and spaced apart side walls 22. An aperture provided in top wall 18 permits the injector 10 to be operatively connected to an SFC column 30. A $CO_2$ tank 32 is attached via hose 34 to a supercritical fluid pump 33, which is connected to injector 10 by stainless steel tubing 35.

Figure 2:
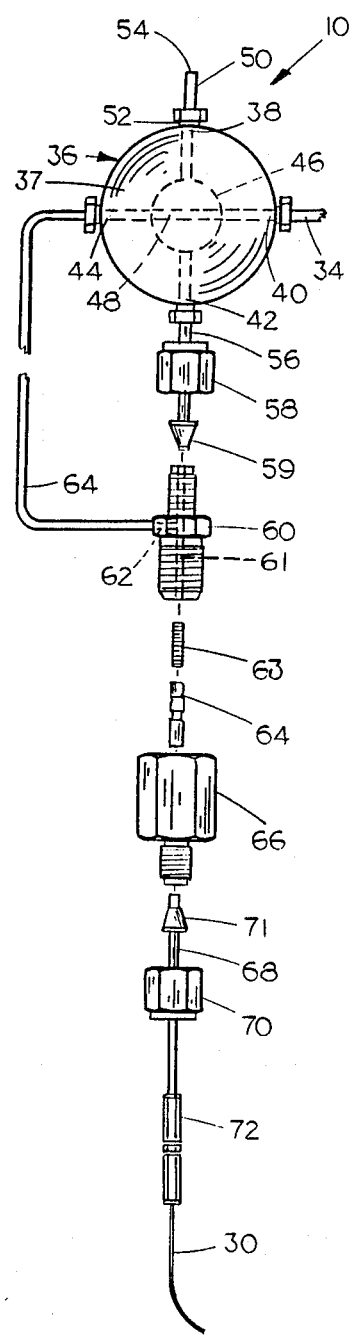
FIG. 2 is an enlarged, exploded view of the present invention.

Referring now to FIG. 2, the injector 10 of the present invention is formed from a switching valve 36. The switching valve includes a body section 37 having four ports 38, 40, 42 and 44 which are in the same plane and are perpendicular to the axis of rotation of a rotor 46. Port 38 registers with port 42 and port 40 registers with port 44. Rotor 46 has a 0.28-in. (0.71-mm) diameter hole 48 drilled therethrough which is perpendicular to the rotor's axis of rotation. Rotor 46 is operable between a first position (loading position), which connects ports 38 and 42, and a second position (chromatographic position) which connects ports 40 and 44. In the preferred embodiment, the switching valve 36 is a Valco Model C4W four-port switching valve.

An upper needle guide 50 has one end 52 thereof operatively secured to port 38 in a conventional manner. End 54 is tapered with a small drill bit so as to facilitate insertion of a GC on-column syringe needle. Upper needle guide 50 functions both as a needle guide and as a positive stop so as to ensure proper positioning of the fused-silica needle during the injection of a sample. A first tubular member 56 has one end thereof operatively secured to port 42 as illustrated in FIG. 2. The opposing end of second tubular member 56 has a nut 58 and a ferrule 59 thereon to threadably and sealably engage a tubing-to-male npt union 60. Upper needle guide 50 and first tubular member 56 are formed from 2.5 cm lengths of 1/16-in. (1.59 mm o.d.) stainless steel tubing having an inner diameter of 0.030-in. (0.76 mm).

The tubing-to-male npt union 60 has a transversely extending aperture 62 drilled therein to communicate with interior passageway 61 as seen in FIG. 2. A bypass tube 64, having a diameter of 1/16-in. (1.59 mm o.d.) has one end thereof operatively secured to port 44 with the opposing end thereof silver-soldered to aperture 62. A needle guide spring 63 and a needle guide 64 are inserted into union 60 with needle guide 64 positioned below needle guide spring 63. A 1/16-in. female npt to 1/16-in. tube union 66 has the female end thereof threadably and sealably connected to the base of tubing-to-male npt union 60. The male-to-female union 66 operatively secures needle guide spring 63 and needle guide 64 within tubing-to-male union 60. The female-to-tubing union 66 was modified by drilling a 1/16-in. diameter hole through the shoulder of the interior of the fitting (not shown) so as to permit a retention gap 68 to pass through the fitting and butt up against the bottom of needle guide 64.

The retention gap 68 is formed from a 7-cm long 1/16-in. o.d. by 300 $\mu$m i.d. glass-lined, stainless steel tube. The retention gap 68 is installed by sliding the tubing through a 1/16-in. nut 70 and a polyamide ferrule 71 until the end of the tubing is pushed gently against needle guide 64. This allows the needle of a conventional GC on-column injection syringe to slide smoothly through the four-port valve and into the retention gap. A low dead volume connector 72 connects the retention gap 68 to capillary SFC column 30. The retention gap end of connector 72 was drilled to a depth of 1-mm with a 1/16-in. drill in order to aid in aligning retention gap 68 with capillary SFC column 30.

The invention 10 is installed on the supercritical fluid chromatograph with the bracket 12 such that the valve is positioned at a height which is 13-cm above the interior of top wall 18 (as measured from the center of the valve body 37). One-quarter inch fiberglass insulation 74 is wrapped around the column between tubing-to-male npt union 60 and top wall 18, to ensure that the temperature of the assembly is maintained at 45° to 50° C.

Figure 5:
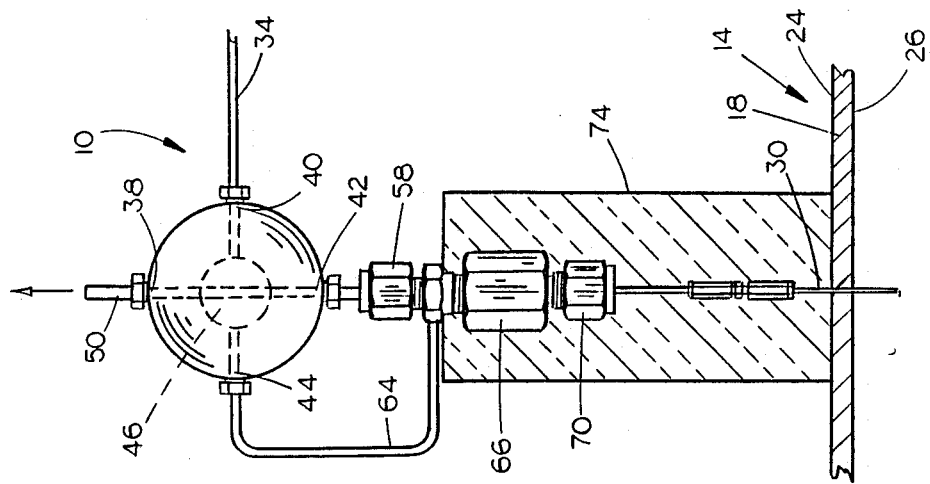
FIG. 5 is a view similar to FIG. 4, but showing the step of venting the solvent.
Figure 4:
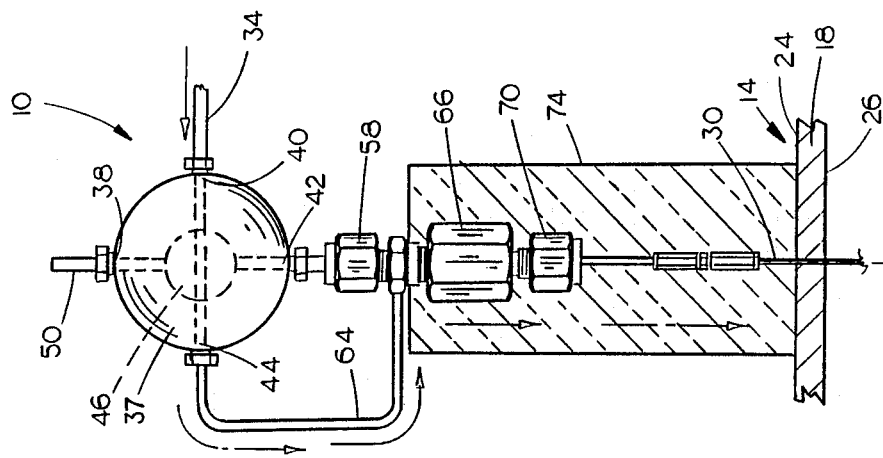
FIG. 4 is a view similar to FIG. 3, but showing the step of moving the injector into a chromatographic position.
Figure 3:
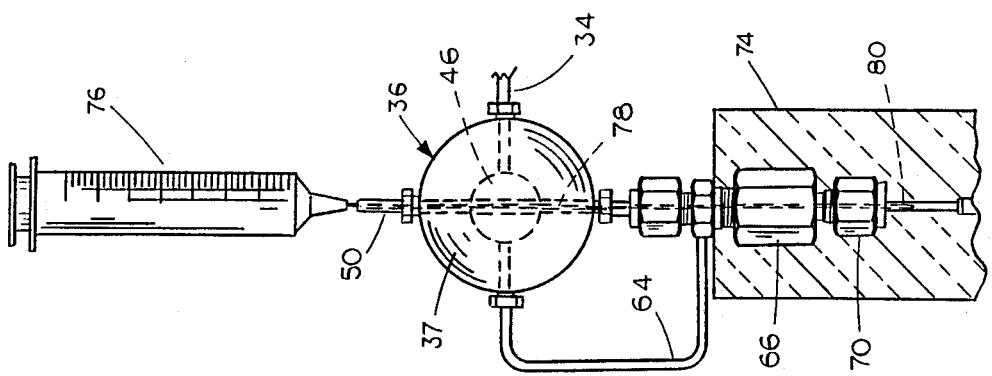
FIG. 3 is an enlarged, elevational view of the invention in which the injector is in a loading position.

The sample injections are performed using a 5-$\mu$L on-column GC syringe 76 which has been fitted with 10-cm long fused silica needle. The sample has a solvent portion and at least one analyte. The technique for performing the injection and accomplishing solvent venting is as follows: (1) The rotor 46 is rotated so that ports 38 and 42 are aligned (loading position) resulting in the release of $CO_2$ pressure from the SFC column 30. See FIG. 3. During the sample loading, the oven temperature is maintained at the temperature used for the SFC analysis (typically 125° C.). (2) The on-column syringe needle 78 is inserted through ports 38 and 42 such that the end 80 of the needle 78 is inserted into the retention gap 68 with the sample being injected 3-cm above the SFC column 30. (3) The on-column syringe needle 78 is withdrawn and the SFC column is immediately pressurized by rotating the rotor 46 to the chromatographic position thereby permitting the carrier (the $CO_2$) to flow from pump 33 to SFC column 30 (see FIG. 4). (4) After 15 seconds the solvent is vented by rotating the rotor 46 to the loading position (see FIG. 5). (5) After venting the solvent for 5 seconds the rotor 46 is returned to the chromatographic position and the SFC separation is performed in a normal manner.

Extensive testing of the present invention, and the method for using the same, revealed that the peak shapes and chromatographic resolutions which were obtained, compared favorably to those that were attained using conventional split injection techniques.

The testing indicated that the solvent venting technique greatly reduced the background from the solvent and resulted in a near zero baseline signal (as compared to the signal before injection) shortly after sample injection. In contrast, the nonvented injections failed to achieve a near zero baseline signal during the entire chromatographic run and an additional hour of flushing the column after the separation was completed was required for the baseline to return to the pre-injection zero level.

The post-injection solvent venting also eliminated the broad solvent peaks normally associated with the splitless SFC injection without causing loss of nonvolatile (greater than $C_{20}$ alkanes) analytes. Because volumes as large as .5 $\mu$L can be injected without the need for sample splitting, more dilute samples can be analyzed and flame ionization detection (FID) limits below 100 pg injected on-column (200 ppb w/v) for alkanes were achieved. Even with the large dilute samples being tested, there was no need for refocusing of the analytes in order to obtain good chromatographic peak shapes. The injector was extensively used with the on-column venting technique and there was no noticeable degradation of the column's performance.

With respect to the alkanes smaller than $C_{20}$, the use of the injector of the present invention did yield broader peaks than were obtained by utilizing conventional split injection techniques, and some loss of alkanes smaller than the $C_{20}$ may occur. It is believed that, in part, the smaller peaks are the result of the difficulty in properly integrating broad peaks rather than a result of their loss during the solvent venting step. While the broad peaks for the lower molecular weight alkanes are obviously not desirable, capillary GC would be the choice to separate such species. The less volatile species, which are of interest for SFC, show good chromatographic peak shapes and no detectable loss using the on-column injector and venting technique described hereinabove. It can therefore be seen that the present invention accomplishes at least the above stated objectives.

We claim:

1. An injector for use with capillary supercritical fluid chromatography (SFC) comprising:
    a switching valve having a body portion and a rotor rotatably mounted within said body portion;
    said body portion having first, second, third and fourth ports spaced about the periphery of said body, said first and third ports being axially aligned and said second and fourth ports being axially aligned;
    said rotor having an opening extending therethrough perpendicular to a central axis of rotation thereof and located for selective registry with said ports, said rotor being rotatable between a loading position wherein said opening registers with said first and third ports to permit the flow of fluid therethrough, and a chromatographic position wherein said opening registers with said second and fourth ports to permit the flow of fluid therethrough;
    means connected to said rotor for operating said rotor between the loading and chromatographic positions;
    a first tubular means having a first end connected to said third portion and a free end extending therefrom for operably connecting said third port to an end of a capillary SFC column, said first tubular means being axially aligned with said first and third ports;
    a second tubular means operably connected for communication between said fourth port and said first tubular means, said connection spaced from the free end of said first tubular means; and
    retention gap means connected to the free end of said first tubular means and axially aligned therewith to permit the introduction of a needle through said first port, rotor opening, third port, first tubular means and into said retention gap means to inject a sample therein for analysis.

2. The injector of claim 1, wherein said rotor is mounted in said body portion to seal and block said first and third ports when in the chromatographic position, and to seal and block said second and fourth ports when in the loading position.

3. The injector of claim 1, further comprising means on said body portion for operably securing a pressurized fluid source to said second port.

4. The injector of claim 1, further comprising a connection means attached to said retention gap means and adapted to secure said retention gap means to a capillary SFC column.

5. An injector for use with capillary supercritical fluid chromatography (SFC) comprising:
    a switching valve having a body portion and a rotor rotatably mounted within said body portion;
    said body portion having first, second, third and fourth ports spaced about the periphery of said body, said first and third ports being axially aligned and said second and fourth ports being axially aligned;
    said rotor having an opening extending therethrough perpendicular to a central axis of rotation thereof and located for selective registry with said ports, said rotor being rotatable between a loading position wherein said opening registers with said first and third ports to permit the flow of fluid therethrough, and a chromatographic position wherein said opening registers with said second and fourth ports to permit the flow of fluid therethrough;
    means connected to said rotor for operating said rotor between the loading and chromatographic positions;
    a first tubular means extending from said third port, said first tubular means being axially aligned with said first and third ports;
    a first fitting having a bore therethrough from an upper to a lower end, said first fitting mounted at its upper end to said first tubular means with said bore in fluid communication therewith;
    a second tubular means operably connected between said fourth port and said first fitting and connected for fluid communication with said bore, said connection spaced from the first fitting and connected for fluid communication with said bore; and
    retention gap means connected to the lower end of said first fitting and axially aligned therewith to permit the introduction of a needle through said first port, rotor opening, third port, first fitting and into said retention gap means to inject a sample therein for analysis.

6. The injector of claim 5, further comprising means mounted within said first fitting bore for guiding a needle into said retention gap means, said needle guide means adapted to permit fluid to flow through said bore from both the second tubular means and the first tubular means.

7. The injector of claim 6, further comprising:
    a second fitting connected to said first fitting means, said second fitting having a hole drilled therethrough adapted to slidably receive said retention gap means therein, said second fitting adapted to secure said needle guide means within said first fitting; and means on said second fitting for selectively retaining said retention gap means therein.

8. A method for analyzing a liquid sample by a capillary supercritical fluid chromatography (SFC) apparatus, comprising the steps of:

providing a capillary SFC analysis apparatus, including:

an oven portion;

a capillary SFC column projecting from said oven portion; and an injector connected to said SFC column, said injector including:

a switching valve having a body portion and a rotor rotatably mounted within said body portion;

said body portion having first, second, third and fourth ports spaced about the periphery of said body, said first and third ports being axially aligned and said second and fourth ports being axially aligned;

said rotor having an opening extending therethrough perpendicular to a central axis of rotation thereof and located for selective registry with said ports, said rotor being rotatable between a loading position wherein said opening registers with said first and third ports to permit the flow of fluid therethrough, and a chromatographic position wherein said opening registers with said second and fourth ports to permit the flow of fluid therethrough;

means connected to said rotor for operating with rotor between the loading and chromatographic positions;

a first tubular means having a first end connected to said third port and a free end extending therefrom for operably connecting said third port to said capillary SFC column, said first tubular means being axially aligned with said first and third ports;

a second tubular means operably connected for communication between said fourth port and said first tubular means, said connection spaced from the free end of said first tubular means; and retention gap means connected to the free end of said first tubular means and axially aligned therewith to permit the introduction of a needle through said first port, rotor opening, third port, first tubular means and into said retention gap means to inject a sample therein for analysis;

positioning said rotor in the loading position;

providing a syringe with sample to be tested therein, and with a needle having a length so as to extend from said first port in said valve through said third port and first tubing means into said retention gap means;

inserting said needle through said first port and into said retention gap means;

loading the sample from the syringe into the retention gap and withdrawing the needle;

rotating said rotor kto said chromatographic position;

pressurizing the SFC column by pumping a carrier fluid into said second port;

rotating said rotor to said loading position to vent solvent after a predetermined amount of time;

rotating said rotor to said chromatographic position after a predetermined period of time; and performing the SFC separation in a conventional manner.

* * * * *